US00PP33356P2

(12) United States Plant Patent
Martinez et al.

(10) Patent No.: US PP33,356 P2
(45) Date of Patent: Aug. 17, 2021

(54) SEEDLESS TABLE GRAPEVINE NAMED 'ITUMFIVE'

(50) Latin Name: *Vitis vinifera*
Varietal Denomination: Itumfive

(71) Applicant: Investigacion y Tecnologia de Uva de Mesa S.L., Blanca (ES)

(72) Inventors: Manuel Tornel Martinez, La Alberca (ES); Juan Carreno Espin, Murcia (ES)

(73) Assignee: Investigacion y Tecnologia de Uva de Mesa S.L.

( * ) Notice: Subject to any disclaimer, the term of this patent is extended or adjusted under 35 U.S.C. 154(b) by 0 days.

(21) Appl. No.: 16/983,915

(22) Filed: Aug. 3, 2020

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205, 206, 207
See application file for complete search history.

(56) References Cited

PUBLICATIONS

UPOV: Pluto Plant Variety Database ; citation for 'ITUMFIVE', Retrieved from the Internet on Jan. 7, 2021. (1 page total).*
Investigacion y Technologia de Uva de Mesa S.L. , Document Identifier AU2017056V, Retrieved East, PTO search engine (1 page total).*

* cited by examiner

*Primary Examiner* — Susan McCormick Ewoldt
(74) *Attorney, Agent, or Firm* — Cassandra Bright

(57) ABSTRACT

A new and distinct variety of grapevine named of 'ITUMFIVE' is herein disclosed. 'Itumfive' abundantly forms medium yellow green seedless berries with an attractive narrow, circular ellipsoid berry shape, a neutral flavor and a very crunchy and firm berry texture. Being a very late season variety, the fruit commonly is ready for harvesting in autumn from September to October in Blanca, Murcia, Spain. 'Itumfive' displays good eating qualities as a table grape, the fruit meatiness and firmness render the fruit amenable for handling, shipping, and storage.

4 Drawing Sheets

Latin name of the genus and species: *Vitis vinifera.*
Variety denomination: 'ITUMFIVE'.

BACKGROUND OF THE INVENTION

A breeding program was initiated during 2003 at a research nursery in Blanca, Murcia, Spain. During the development of this breeding program, a new variety of *Vitis vinifera* was created by deliberate cross breeding of two parent plants by emasculation of the pollen bearing organ of the female and introducing pollen from another male origin. The female parent of the new variety is 'ITUM 91-89-56', an unpatented proprietary selection. The male parent (i.e. the pollen parent) of the new variety is 'Princess', unpatented.

'Itumfive' was identified as a potentially interesting selection during 2006 at the same location in Murcia, Spain. After identifying the new variety as a potentially interesting selection, first propagation of 'Itumfive' by vegetative cuttings was undertaken during 2006, at the research nursery in Murcia, Spain. Controlled testing and propagation of the new variety continued, to assess stability of the unique characteristics of this variety. Subsequently, several generations have been reproduced and have shown that the unique features of this cultivar are stable and reproduced true to type. No publications have been issued on the plant breeding invention. Date of first sale was Sep. 2, 2019, occurring in Spain. This sale was made directly by the inventor or one who obtained the claimed invention directly or indirectly from the inventor. This sale and all public disclosures made between Sep. 2, 2019 and the filing of this application fall within the exception allowed under 102(b)(1).

SUMMARY OF THE INVENTION

The cultivar 'ITUMFIVE' has not been observed under all possible environmental conditions. The phenotype may vary somewhat with variations in environment such as temperature, day length, and light intensity, without, however, any variance in genotype. The new variety 'Itumfive' is yellow green seedless table grape with medium production and a medium fertility index "0, 8". In addition to the before mentioned characteristics, the following traits have been repeatedly observed and are determined to be the unique characteristics of 'Itumfive' These characteristics in combination distinguish 'Itumfive' as a new and distinct *Vitis* cultivar:

1. Individual fruit with medium yellow green skin coloration; formed in medium-to-large clusters.
2. An attractive circular ellipsoid berry shape.
3. A very late season variety, commonly bears fruit for harvesting from September to October in the region of Murcia, Spain.
4. Very firm berry and very crunchy fruit texture.
5. Absence of seeds.
6. Resistance to cracking.
7. Fruit has been found to be suitable for handling and shipping.
8. Observed tolerance of water shortage.

9. Observed tolerance for temperatures up to 41° C.
10. Neutral flavor profile.

COMPARISON TO PARENT VARIETIES

TABLE 1

| Characteristic | 'Itumfive' | Parental A (fem) ITUM '91-89-56' |
|---|---|---|
| Berry Texture | Very firm | Moderate firm to soft |
| Berry Flavor: | Neutral | Neutral |
| Formation of Seeds | Seedless | Rudimentary |

| Characteristic | 'Itumfive' | Parental B (masc.) 'Princess' |
|---|---|---|
| Berry Flavor: | Neutral | Muscat |
| Formation of Seeds | seedless | Rudimentary |
| Berry Shape: | Narrow circular ellipsoid | Ovoid |

COMMERCIAL COMPARISON

TABLE 2

| Characteristic | 'Itumfive' | 'Amgrapone' (unpatented) |
|---|---|---|
| Berry Flesh Texture | Very firm | Moderately firm |
| Formation of Seeds | Seedless | rudimentary |
| Ripening Time | Very late | Late |

| Characteristic | 'Itumfive' | 'Sultanina' (unpatented) |
|---|---|---|
| Berry texture | Very firm | Moderately firm to soft |
| Mature leaf: arrangement of lobes of petiole sinus | Slightly open | Slightly overlapped |

BRIEF DESCRIPTION OF THE PHOTOGRAPHS

The accompanying photographic illustration shows typical samples of vegetative growth of a 12 year old specimens of the new variety, in color as nearly true as it is reasonably possible to make in a color illustration of this character. Plants were grown in Murcia, Spain. Colors in the photograph may differ from the color values cited in the detailed botanical description below, which accurately describes the colors of the new Grapevine.

DETAILED BOTANICAL DESCRIPTION

Figure 1:
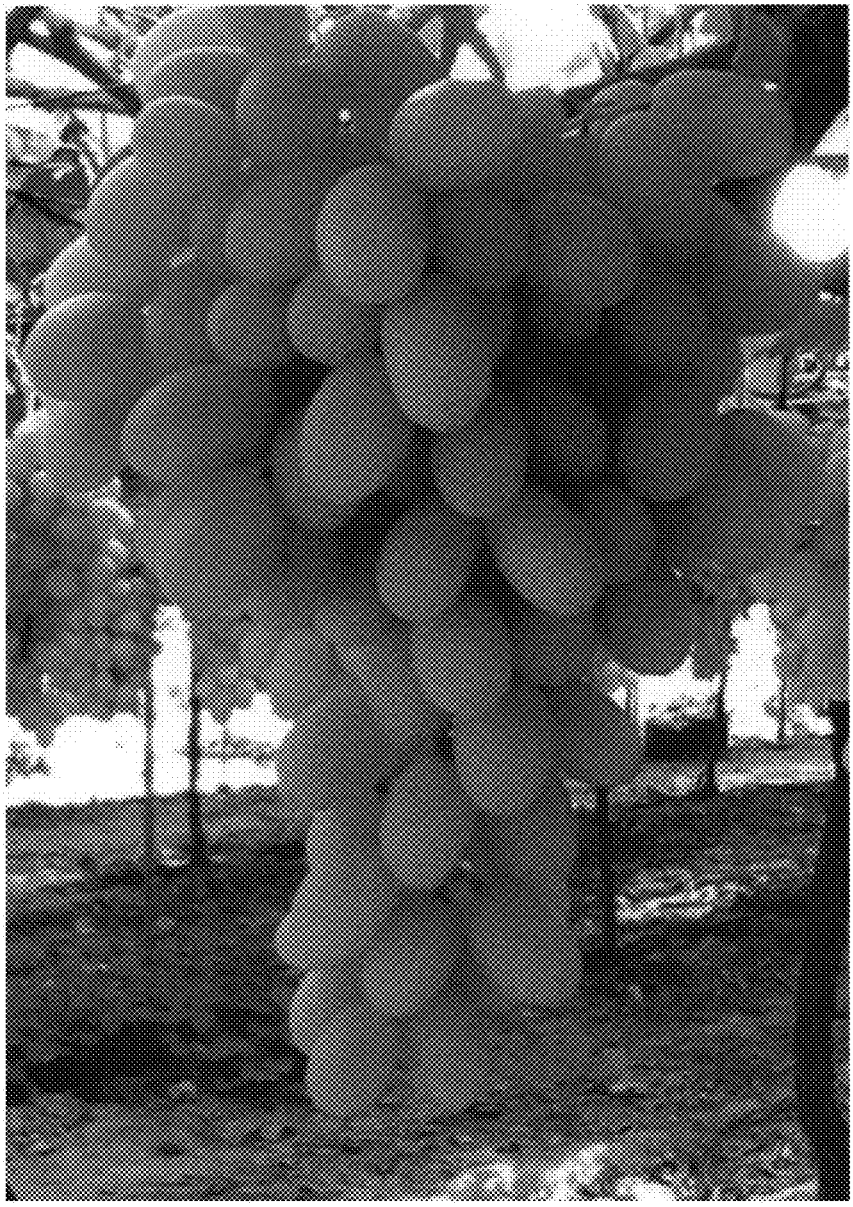
FIG. 1 illustrates a fruit cluster of 'Itumfive'.
Figure 2:
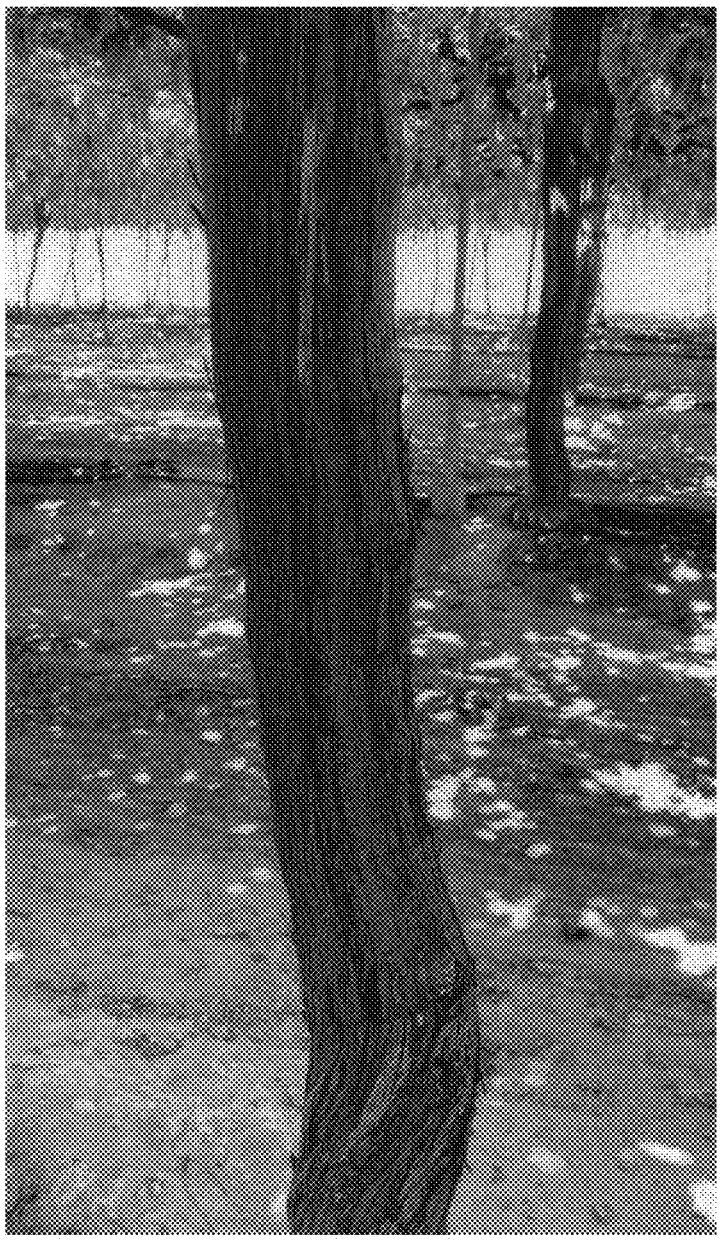
FIG. 2 shows a close-up view of the trunk of 'Itumfive'.
Figure 3:
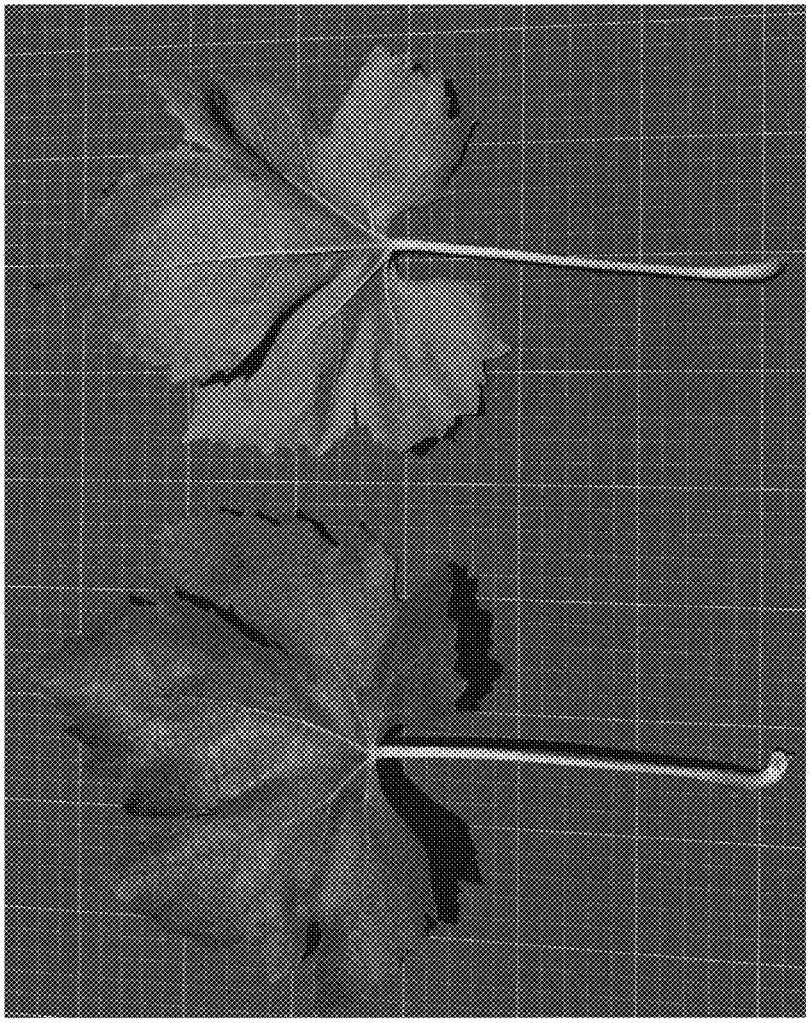
FIG. 3 illustrates in close up perspective typical foliage of the new variety, both front and back of the leaf.
Figure 4:
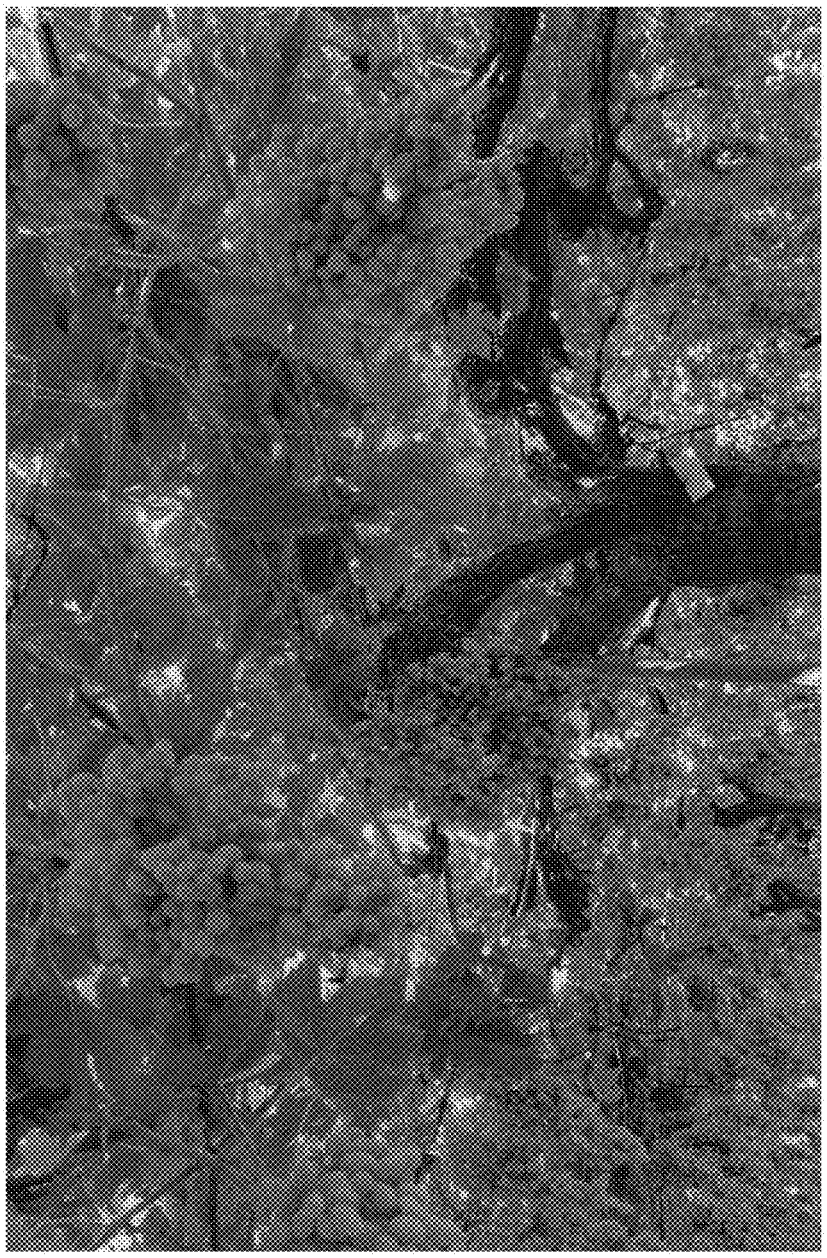
FIG. 4 illustrates the plant canopy of 'Itumfive', including fruits, branches and foliage.

In the following description, color references are made to The Royal Horticultural Society Colour Chart 2015 except where general terms of ordinary dictionary significance are used. Some descriptors, when useful have been incorporated from *UPOV Grape Descriptor Guidelines*. The description is based on the observation of plants growing on '1103 Paulsen' rootstock in clay stony soil conditions in the fields near Blanca, Murcia, Spain. The age of plant described is of 12 years, with an average height of 200 cm, a high canopy density, a 300 cm plant spread, a one-year growth rate to reach two meters high and 20 to 30 days to initiate roots at approx. 20° C. At observation location temperature ranged between 15° C. to 35° C. during the day, and between 5° C. to 20° C. during the night.

Botanical classification: *Vitis vinifera* 'Itumfive'.

CANES

Characteristics of mature canes:
- *Diameter.*—1.6 to 1.8 cm.
- *Length.*—70-80 cm.
- *Color.*—Medium light brown (164C RHS).
- *Cross section shape.*—Circle.
- *Strength.*—Medium.
- *Texture.*—Non-pubescent, rough.

Lenticels:
- *Diameter.*—<0.5 mm.
- *Density.*—Few to-moderate.
- *Color.*—Medium light brown (164C RHS).

Internode:
- *Length.*—8-12 cm; midpoint 10 cm.
- *Pigmentation at internode, dorsal.*—Near RHS Greyed-Orange 164C).
- *Pigmentation at internode, ventral.*—Near RHS Greyed-Orange 164C).

Tendril pattern (counting nodes/buds from the base of the branch to its end, when a tendril is present, a 1 is marked, no tendril, a 0 is marked) on show: 0,0,0,0,0,0,1.
- *Tendrils forked.*—Yes.
- *Tendril texture.*—Glabrous.
- *Tendril length.*—10 cm.

Bud:
- *Width.*—1.3 cm.
- *Bud length.*—0.4 cm.
- *Bud shape.*—Triangular.
- *Bud color.*—Light yellow brown Near RHS Greyed-Yellow 161D, flushed 162D.

Young shoot:
- *Openness of tip.*—Open. Anthocyanin not present in Shoot pigmentation.
- *Texture.*—Smooth.
- *Diameter.*—0.8 to 1.2 cm.
- *Longitudinal Length.*—1.4-3.5 m; midpoint 2.0 m.
- *Color.*—Near RHS Greyed-Orange 164D, streaked 165D.
- *Cross section.*—Circular.
- *Strength.*—Medium.
- *Attitude.*—Erect.
- *Bark texture.*—Shaggy.
- *Bark color.*—Near RHS Greyed-Red 178A streaked 180A.

FOLIAGE

Leaf:
- *Arrangement.*—Alternate.
- *Quantity.*—Approximately 16 per cane.
- *Average length.*—21 cm.
- *Average width.*—19 cm.
- *Overall shape of blade.*—Broad obovate.

*Apex*.—Acute.
*Base*.—Rounded.
*Margin*.—Shallow dentations.
*Texture of top surface*.—Smooth.
*Texture of bottom surface*.—Smooth.
*Pubescence*.—None.
*Aspect*.—Undulate.

Sinuses:
*Shape of petiolar sinus*.—High widened.
*Shape of base petiolar sinus*.—High widened.
*Depth of petiolar sinus*.—6 cm.
*Width of petiolar sinus*.—2 cm.
*Shape of upper sinuses*.—High widened.

Color:
*Immature foliage upper side*.—Near RHS Yellow-Green 154D streaked 150D.
*Immature foliage under side*.—Near RHS Yellow-Green 154D streaked 150D.
*Mature foliage upper side*.—Near RHS Green 137A.
*Mature foliage under side*.—Near RHS Yellow-Green 144A.

Venation:
*Type*.—Pinnate.
*Venation color upper side*.—Near RHS Yellow-Green 154C.
*Venation color under side*.—Near RHS Yellow-Green 154C.

Petiole:
*Length*.—17 cm.
*Diameter*.—0.4 cm.
*Color*.—Near RHS Yellow-Green 144A) with weak Anthocyanin presence near base, Greyed-Red 178C.
*Texture*.—Glabrous.

FLOWER

Flowering period begins around May, 16 to 24 in Murcia, Spain.

Inflorescence when in bud:
*Length*.—16 cm.
*Diameter*.—7 cm.
*Bud color*.—Near RHS Green 140B.
*Bud shape*.—Conical.
*Bud size*.—About 1 to 2 mm by 1 to 2 mm.

Individual flower:
*Main time of flowering*.—8 days.
*Size of entire flower* (*to end of stamens*).—0.7 cm.
*Calyx shape*.—Funnel.
*Calyx size*.—1.5 cm.
*Calyx color*.—Near RHS Green 140A.
*Calyx apex*.—Rounded.
*Calyx base*.—Rounded.
*Calyx texture*.—Glabrous all surfaces.
*Diameter*.—15 mm.
*Quantity per flowering stem*.—5.
*Days lasting on plant*.—8 days.

Petals:
*Quantity*.—5.
*Arrangement*.—Symmetrical rotate.
*Length*.—0.2 cm.
*Width*.—<0.1 cm.
*Shape*.—Obovate.
*Apex*.—Ovate.
*Base*.—Ovate.
*Texture, upper and lower surfaces*.—Soft.
*Color*.—At opening upper surface: Near RHS Green 140B. At opening lower surface: Near RHS Green 140B. Fully opened upper Surface: Near RHS Green 140B.

Peduncles:
*Fruit peduncle length*.—70 mm.
*Fruit peduncle width*.—6 mm.
*Angle*.—About 80° to the lateral branch.
*Fruit peduncle strength*.—Firm-hard.
*Fruit peduncle texture*.—Soft.
*Color*.—Light green (142D RHS).

Pedicels:
*Length*.—0.6 cm.
*Diameter*.—0.05 cm.
*Angle*.—About 80° to center of flower cluster.
*Strength*.—Medium.
*Texture*.—Softly pubescent.
*Color*.—Near RHS Green 141C.

Fragrance: Absent.

REPRODUCTIVE ORGANS

Number of stamens: 5.

Anthers:
*Shape*.—Oblong.
*Length*.—Approximately 0.1 cm.
*Color*.—Near Yellow 9C.

Pollen:
*Color*.—Near Yellow 8A.

Quantity: Abundant.

Pistil:
*Quantity*.—1.
*Length*.—0.25 cm.

Style:
*Length*.—<0.1 cm.
*Color*.—Near RHS Green 143C.

Stigma:
*Shape*.—Round.
*Color*.—Near RHS Yellow-Green 144D.

Ovary color: Near RHS Yellow-Green 144D.

FRUIT

Cluster:
*Average length*.—31 cm.
*Average diameter*.—20 cm.
*Average weigh*.—800 grams.
*Fertility index*.—Number of clusters per sprouted buds 0,8.

Fruit:
*Average length*.—3.2 cm.
*Average diameter*.—2.4 cm.
*Shape*.—Narrow circular ellipsoid.
*Cross-section*.—Circular.
*Color of berry skin*.—Near RHS Yellow-Green 150A.
*Color of berry flesh*.—Translucent, near White 155B.
*Brix at harvest*.—18.
*Ease of detachment from pedicle*.—Difficult, well hooked and difficult detachment.
*Thickness of skin*.—Thin.
*Firmness of flesh*.—Very crunchy and firm.
*Particular flavor*.—Neutral.
*Formation of seeds*.—None. Seeds are absent in this variety.
*Average weight of an individual berry*.—9.1 grams.

*Storage characteristics*.—Typically and observed 90 days at 1° C.

OTHER CHARACTERISTICS

Disease and pest resistance: Not observed to be susceptible nor resistant to normal diseases and pests of *Vitis vinifera*.

Temperature tolerance: Observed growing between 6° C. to 41° C.

Drought tolerance: Observed to tolerate water shortages during the dry Summer months of Murcia, Spain without detriment.

What is claimed is:

1. A new and distinct cultivar of *Vitis* grapevine named 'ITUMFIVE' as herein illustrated and described.

* * * * *